(12) United States Patent
Peralta

(10) Patent No.: US 12,077,451 B2
(45) Date of Patent: Sep. 3, 2024

(54) METHOD FOR PRODUCING A LITHIUM-CONTAINING METAL OXIDE THAT CAN BE USED AS AN ACTIVE MATERIAL FOR A POSITIVE ELECTRODE

(71) Applicant: COMMISSARIAT À L'ENERGIE ATOMIQUE ET AUX ÉNERGIES ALTERNATIVES, Paris (FR)

(72) Inventor: David Peralta, Grenoble (FR)

(73) Assignee: COMMISSARIAT À L'ÉNERGIE ATOMIQUE ET AUX ÉNERGIES ALTERNATIVES, Paris (FR)

( * ) Notice: Subject to any disclaimer, the term of this patent is extended or adjusted under 35 U.S.C. 154(b) by 765 days.

(21) Appl. No.: 17/252,906

(22) PCT Filed: Jun. 18, 2019

(86) PCT No.: PCT/FR2019/051484
§ 371 (c)(1),
(2) Date: Dec. 16, 2020

(87) PCT Pub. No.: WO2019/243729
PCT Pub. Date: Dec. 26, 2019

(65) Prior Publication Data
US 2021/0261434 A1    Aug. 26, 2021

(30) Foreign Application Priority Data
Jun. 18, 2018    (FR) ...................................... 1855347

(51) Int. Cl.
*C01G 53/00*    (2006.01)
*C01G 45/12*    (2006.01)
(Continued)

(52) U.S. Cl.
CPC ......... *C01G 53/42* (2013.01); *C01G 45/1228* (2013.01); *C01G 51/42* (2013.01);
(Continued)

(58) Field of Classification Search
None
See application file for complete search history.

(56) References Cited

FOREIGN PATENT DOCUMENTS

CN    104307482 A  *  1/2015
CN    104577097 A  *  4/2015
(Continued)

OTHER PUBLICATIONS

Song et al., Metal/metal oxide nanostructures derived from metal-organic frameworks, RSC Adv., 2015, 5, 7267-7279 (Year: 2015).*
(Continued)

*Primary Examiner* — Lucas J. O'Donnell
(74) *Attorney, Agent, or Firm* — Pearne & Gordon LLP

(57) ABSTRACT

A method for producing a lithium-containing oxide comprising one or more metal elements, which can be used as an active material for an electrode, for example a positive electrode for a lithium battery, the method comprising the following successive steps: a) a step of bringing at least one coordination polymer into contact with a lithium source, the coordination polymer comprising the other metal element(s) interconnected by organic ligands; b) a step of calcining the mixture resulting from step a).

20 Claims, 4 Drawing Sheets

(51) Int. Cl.
*C01G 51/00* (2006.01)
*H01M 10/0525* (2010.01)

(52) U.S. Cl.
CPC ..... *H01M 10/0525* (2013.01); *C01P 2002/74* (2013.01); *C01P 2002/77* (2013.01)

(56) References Cited

FOREIGN PATENT DOCUMENTS

| | | | |
|---|---|---|---|
| CN | 106876693 A | | 6/2017 |
| CN | 108336308 A | * | 7/2018 |
| EP | 3331064 A1 | | 6/2018 |
| JP | 2013040119 A | | 2/2013 |
| WO | 2011132147 A1 | | 10/2011 |

OTHER PUBLICATIONS

Metal-Organic-Framework-Based Materials as Platforms for Renewable Energy and Environmental Applications to Zhang et al., Joule 1, 77-107, Sep. 6, 2017 (Year: 2017).*

Search Report for French application No. FR 1855347 dated Feb. 18, 2019.
International Search Report for PCT/FR2019/051484 dated Nov. 27, 2019.
Written Opinion for PCT/FR2019/051484 dated Nov. 27, 2019.
International Preliminary Report on Patentability for PCT/FR2019/051484 dated Oct. 6, 2020.
Du, Mengjuan et al. "Porous nanostructured ZnCo2O4 derived from MOF-74: Highperformance anode materials for lithium ion batteries", Journal of Energy Chemistry, Jul. 1, 2017, vol. 26, No. 4, pp. 673-680.
Ogihara, Nobuhiro et al: "Organic Dicarboxylate Negative Electrode Materials with Remarkably Small Strain for High-Voltage Bipolar Batteries", Angewandte Chemie International Edition, Sep. 4, 2014, vol. 53, No. 43, pp. 11467-11472.
Tang, Jing et al: "Thermal Conversion of core-Shell Metal Organic Frameworks: A New Method for Selectively Functionalized nanoporous Hybrid Carbon" Journal of the American Chemical Society, Jan. 27, 2015, vol. 137, No. 4, pp. 1572-1580.

* cited by examiner

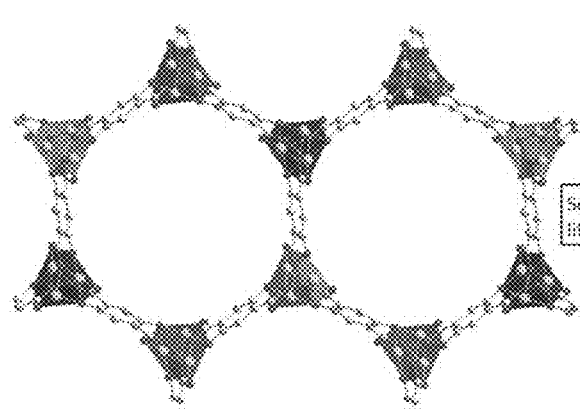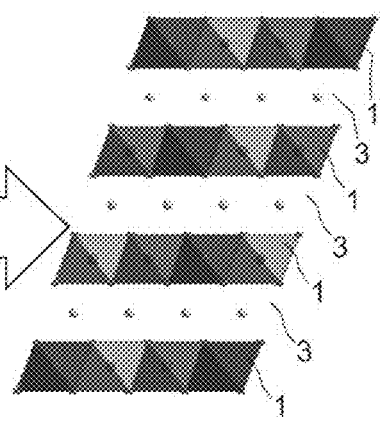
FIG.1A  FIG.1B
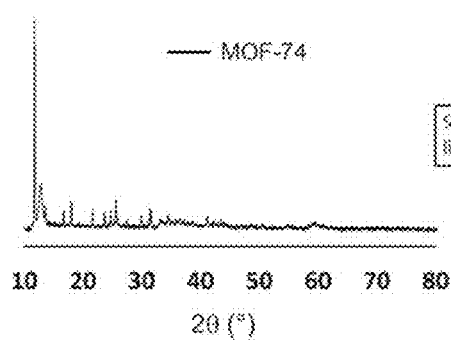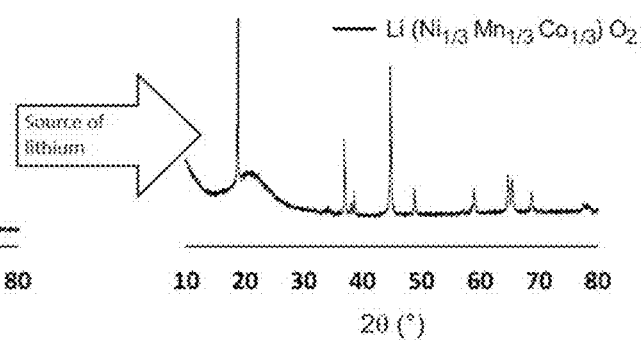
FIG.1C  FIG.1D
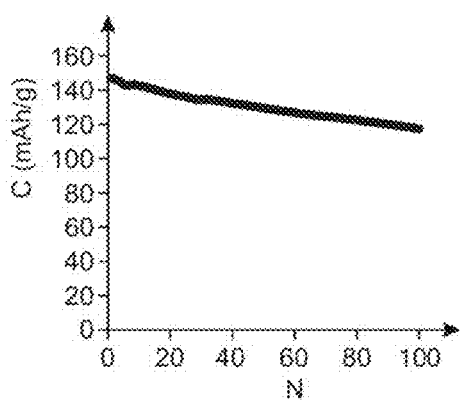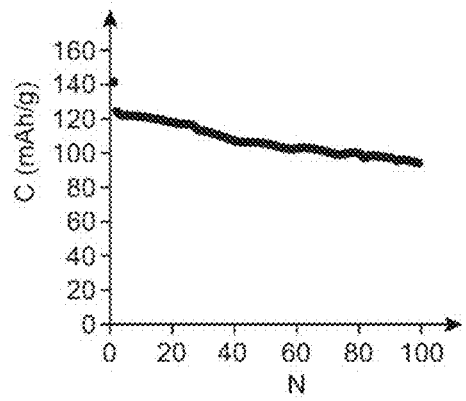
FIG.1E  FIG.1F

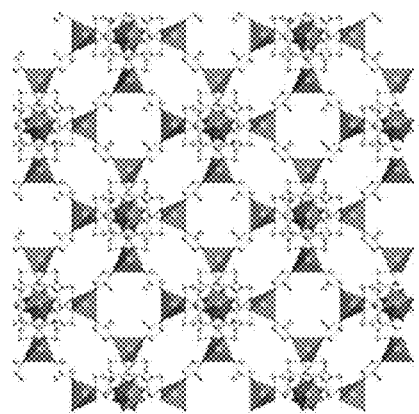 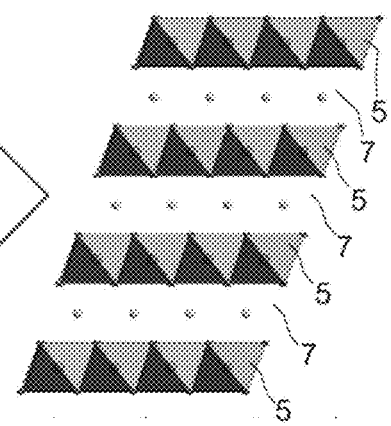
FIG.2A  FIG.2B
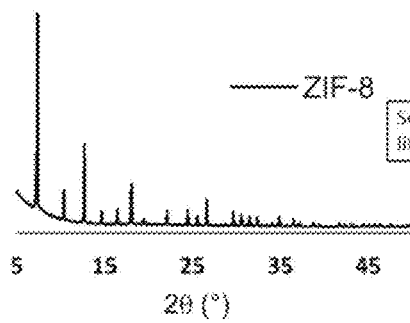 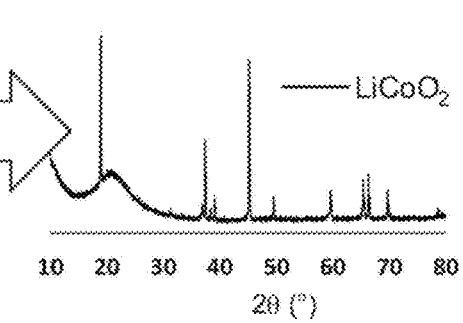
FIG.2C  FIG.2D
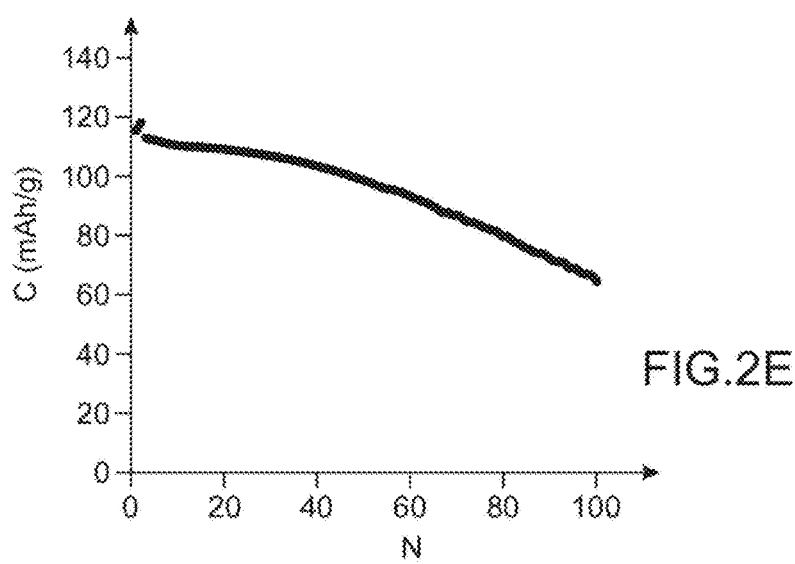
FIG.2E

METHOD FOR PRODUCING A LITHIUM-CONTAINING METAL OXIDE THAT CAN BE USED AS AN ACTIVE MATERIAL FOR A POSITIVE ELECTRODE

CROSS-REFERENCE TO RELATED APPLICATIONS

This is a National Stage application of PCT international application PCT/FR2019/051484, filed on Jun. 18, 2019, which claims the priority of French Patent Application No. 1855347, filed Jun. 18, 2018, both of which are incorporated herein by reference in their entirety.

TECHNICAL FIELD AND PRIOR ART

The present invention relates to a method for producing a lithium-containing metal oxide that can be used as an active material for a positive electrode in a lithium battery, and more specifically in a lithium-ion type battery.

Lithium-ion batteries are of particular interest in fields where autonomy is an essential criterion, as is the case in the field of mobile devices (such as mobile phones, laptops) or the field of transport such as electric vehicles, hybrid vehicles, or even the fields of medicine, space or microelectronics.

From a functional point of view, lithium-ion batteries are based on the intercalation-deintercalation principle of lithium within the constituent materials of electrodes of electrochemical cells of the battery.

More precisely, the reaction which originates the production of current (i.e., when the battery is in discharge mode) risks the transfer, by means of an electrolyte conductor of lithium ions, of lithium cations from a negative electrode which have inserted themselves into the acceptor network of the positive electrode, whereas electrons from the reaction at the negative electrode will feed the external circuit, to which the positive and negative electrodes are connected.

In lithium-ion batteries, the most critical and the most limiting element proves to be the positive electrode and, more specifically, the active material of the positive electrode. Indeed, it is the properties of the active material of the positive electrode that will determine the energy density, the voltage and the lifetime of the battery.

One of the main active materials of the positive electrode used is a lithium-containing oxide from the family of lamellar oxides: $LiCoO_2$, which has high energy density, a long lifetime (greater than 500 cycles) and makes it possible, in couple, with a graphite type active material at the negative electrode to provide a significant voltage (in particular, in the order of 3.6 V), the main disadvantage being its cost which is associated with the use of cobalt. In addition, alternatives have been proposed for reducing the quantity of cobalt used by proposing mixed oxides of the type $Li(Ni,Co,Mn)O_2$ (such as $Li(Ni_{1/3}Mn_{1/3}Co_{1/3})O_2$ also known as NMC) or Li(Ni, Co, Al)$O_2$ (such as $Li(Ni_{0.8}Co_{0.15}Al_{0.05})O_2$ also known as NCA).

These lithium-containing oxide type materials can be prepared by different methods.

For example, for a lithium-containing oxide based on manganese, cobalt and nickel, the latter can be prepared by a method involving co-precipitation in which:

a solution of nickel, manganese and cobalt sulphates is precipitated with a soda or carbonate solution, such that a mixed hydroxide or a carbonate is produced comprising nickel, manganese and cobalt;

the mixed hydroxide or carbonate obtained is calcined at temperatures above 700° C. with a source of lithium (for example, LiOH, $Li_2CO_3$) so as to form the desired oxide.

In a variant of a co-precipitation method, a so-called "all solid" method can be used, wherein a carbonate comprising the different metal elements to be incorporated into the desired oxide or a mixture of carbonates each comprising one of the metal elements to be incorporated into the desired oxide is mixed intimately with a source of lithium, the resulting mixture being then calcined at temperatures above 700° C.

In addition, in view of what exists already, the authors of the present invention have set themselves the objective of proposing a method for producing a lithium-containing oxide comprising one or more other metal elements which are simple to use and do not require complex and expensive equipment, which makes it possible to obtain specific and controlled morphologies (for example, in phase with a use of the oxide obtained in this way as an insert material of lithium) and which can be used in a method for recycling a used material (for example, a method for recycling an active material of an electrode of the lithium-containing oxide type based on one or more other metal elements).

DESCRIPTION OF THE INVENTION

This objective is achieved by a method for producing a lithium-containing oxide comprising one or more other metal elements which can be used as an active electrode material, for example, positive for a lithium battery, said method comprising the following successive steps:

a) a step of contacting at least one coordination polymer comprising the metal element or other metal elements joined together by organic ligands with a source of lithium;

b) a step of calcination of the mixture from step a).

In the above and in the following, a coordination polymer is defined as an organometallic periodic assembly formed by iteration of metal centres (formed in our case by the metal element or other metal elements) joined together by molecules establishing coordination bonds with the metal centres (these molecules being the ligands). More specifically, in our case, the coordination polymer is formed by the metal element or other metal elements in cationic form joined together by means of organic groups borne by the organic ligands, these organic groups establishing coordination bonds with the metal element or other metal elements (which groups can be described as complexing groups). Its properties (form, porosity and specific surface) are a function of the choice of the constituent ligand or ligands of the coordination polymer. In addition and in place of the term "coordination polymer" it is possible to use the term "metal-organic framework", (the abbreviation MOF also being used to denote this type of framework).

The invention differs fundamentally from the prior art in that the lithium-containing oxide comprising one or more other metal elements is obtained from a coordination polymer which is subjected to a calcination step in the presence of a source of lithium, which permits, advantageously, in a single step, the suppression of the organic part of the coordination polymer and the formation of the thus desired lithium-containing oxide.

The metal element or other metal elements of the lithium-containing oxide prepared according to the method of the invention can be selected from the transition metal elements (such as manganese, cobalt, nickel and mixtures of the latter), post-transition metal elements (such as aluminium) and mixtures of the latter. More specifically, the metal element or metal elements can be selected from manganese, cobalt, nickel and mixtures thereof. If the lithium-containing oxide includes a single other metal element, it can be denoted as a monometal lithium-containing oxide and if it includes several other metal elements, it can be a multimetal lithium-containing oxide.

Specifically, the lithium-containing oxides which can be obtained by means of the method of the invention can be:

lamellar oxides of formula $LiMO_2$, where M can be Co, Ni, Mn, Al and mixtures of the latter, such as $LiCoO_2$, $LiNiO_2$, $Li(Ni,Mn,Co)O_2$, $Li(Ni,Co,Mn,Al)O_2$;

oxides with a spinel structure, such as $LiMn_2O_4$.

These lamellar or spinel structure lithium-containing oxides are good candidates for forming the active materials of the positive electrode designed to enter the constitution of lithium batteries. It is understood that a positive electrode is the electrode which serves as the cathode, when the battery discharges current (i.e., when it is in discharge process) and which serves as an anode when the battery is in charging process.

Firstly, the method of the invention comprises a step a) of contacting at least one coordination polymer comprising the metal element or other metal elements joined together by organic ligands with a lithium source.

Advantageously, the organic ligands comprise at least two groups establishing coordination bonds with the metal element or other metal elements, the coordination bonds being established, conventionally, between the free doublets and/or negative charges borne by these groups. This ligand or ligands can be described as polydentate ligands (due to the fact that they comprise several groups establishing coordination binds with the metal element or metal elements) and more specifically, bidentate ligands, when they comprise two of these groups, tridentate ligands when they comprise three of these groups or tetradentate ligands when they comprise four of these groups.

Advantageous organic ligands include:

a first type of ligands consisting of organic ligands comprising at least two groups selected from —COOR groups, OH groups and combinations of the latter, with R representing a hydrogen atom or a monovalent cation, for example, an alkali element cation (in this latter case, the organic ligands can be described as carboxylate ligands);

a second type of ligands consisting of aromatic compounds comprising at least one cycle comprising at least two nitrogen atoms; or mixtures of the latter.

Organic ligands of the first type can advantageously include aromatic compounds comprising at least one cycle comprising at least two groups selected from —COOR groups, —OH groups and combinations of the latter, R being as defined above. By way of example, they can include organic ligands from the family of terephthalic acids and, more specifically, from the family of hydroxyterephthalic acids, such as for example, 2,5-dihydroxyterephthalic acid (referred to by the abbreviation 2,5-dht) with the following formula (I):

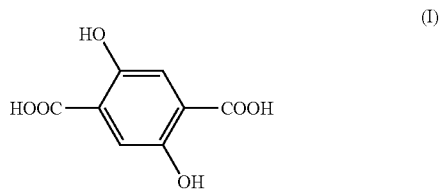 [SMILES: O=C(O)c1cc(O)c(C(=O)O)cc1O]

In particular, this type of ligand is particularly suitable for forming a coordination polymer with at least one metal element selected from cobalt, nickel, manganese and mixtures of the latter. More specifically, the 2,5-dhtp ligand mentioned above is suitable for forming a coordination polymer with at least one bivalent cation (for example, a cobalt cation, a manganese cation, a nickel cation and mixtures of the latter), this coordination polymer being referred to as MOF-74.

The ligands of the second type may include:

monocyclic aromatic compounds with five members comprising two nitrogen atoms (in other words, diazole compounds);

bicyclic aromatic compounds, one of the cycles being a cycle with five members including two nitrogen atoms;

monocyclic aromatic compounds with six members comprising two nitrogen atoms or three nitrogen atoms; or mixtures thereof.

These compounds can also comprise one or more substitutes (for example, an alkyl group) in terms of the carbon atoms or cycles.

For monocyclic aromatic compounds with five members comprising two carbon atoms, particularly advantageous compounds are imidazole compounds, in particular, those corresponding to at least one of the following formulae (II) to (V):

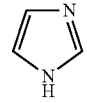
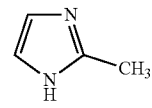
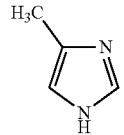
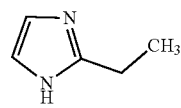

these compounds being referred to respectively as imidazole (for the compound of formula (II)), 2-methylimidazole (for the compound of formula (III)), 4-methylimidazole (for the compound of formula (IV)) and 2-ethylimidazole (for the compound of formula (V)).

For bicyclic aromatic compounds, one cycle of which is a cycle with five members including two nitrogen atoms, particularly advantageous compounds are benzimidazole compounds and, in particular, the compound corresponding to the following formula (VI):

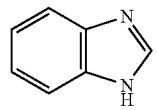
(VI)

For monocyclic aromatic compounds with six members comprising two nitrogen atoms, particularly advantageous compounds can correspond to the following formulae (VII) to (IX):

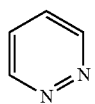
(VII)

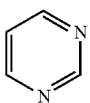
(VIII)

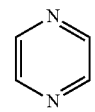
(IX)

these compounds being referred to as pyridazine (for the compound of formula (VII)), pyrimidine (for the compound of formula (VIII)) and pyrazine (for the compound of formula (IX)).

For the monocyclic aromatic compounds with six members comprising three nitrogen atoms, particularly advantageous compounds can correspond to one of the following formulae (X) to (XII):

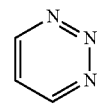
(X)

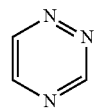
(XI)

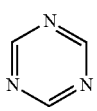
(XII)

These specific ligands of the second type are, in particular, able to form a coordination polymer with cobalt and, in particular, imidazole compounds which can be formed with a divalent cation, such as cobalt, a coordination polymer with a zeolitic framework known as ZIF (ZIF the abbreviation for "Zeolitic Imidazolate Frameworks"). More particularly, the aforementioned 2-methylimidazole of formula (III) can form a coordination polymer with the cobalt denoted as ZIF-8.

The coordination polymer is contacted, according to step a), with a source of lithium. In particular, the source of lithium can be a lithium salt, such as lithium carbonate, lithium hydroxide or lithium acetate. The source of lithium is used, advantageously, in excess relative to the coordination polymer(s), for example, an excess of up to 5 mol % relative to the stoichiometric quantity.

The mixture from step a) is then subjected to a calcination step, so as to form lithium-containing oxide comprising the metal element or other metal elements.

Of course, the temperature and the duration of calcination are selected by a person skilled in the art so as to obtain the oxide phase in the desired crystallised form, this temperature and duration can be easily determined by the person skilled in the art by prior testing to determine as a function of the research phase (the latter being detectable by X-ray diffractometry) the appropriate temperature duration.

By way of example, the calcination step can be performed at a temperature ranging from 700° C. to 1000° C., and preferably from 800° C. to 1000° C. for a period ranging from 12 hours to 24 hours. Preferably, this calcination step is performed in the open air or in a controlled oxygen atmosphere.

It should be noted that it is possible to conserve, during the calcination step, the morphology of the coordination polymer, or in other words the lithium-containing oxide obtained from the method of the invention has a similar morphology to that of the coordination polymer present in the mixture. Thus, particular morphologies of lithium-containing oxide can be obtained according to the method of the invention by choosing to use a coordination polymer with the desired morphology.

Prior to step a), the method of the invention can also comprise a step of preparing the coordination polymer or polymers used in step a), this preparation step can comprise the following operations:

a1) preparation of a solution comprising at least one solvent and the metal element or other metal elements;
a2) addition of the organic ligand or ligands to the solution obtained from the operation a1);
a3) heating the mixture obtained from operation a2).

The solvent used in operation a1) can be an organic solvent, water or a mixture of the latter (for example, a mixture of a protic non-polar solvent, such as dimethylformamide, and water).

Advantageously, the metal element or other metal elements of operation a1) are obtained by dissolving a metal salt or a mixture of metal salts in the solvent. The counterion of the metal salt can be an inorganic ion, for example, a nitrate, a carbonate, a chloride, or a sulphate, or an organic ion, for example an acetate.

According to another advantageous variant, the metal ion or ions of operation a1) can be obtained by dissolving a metal, an alloy of several metals, a metal oxide, or a lithium-containing metal oxide.

For example, according to this last variant, the metal ion or ions of the operation a1) can be obtained by dissolving a used material comprising the metal element or said metal elements, this used material may be a used active material from a battery or a catalyst. In any case, in a general manner, any material containing types of metal to be recovered, for example cobalt, nickel, manganese, and/or iron can be recycled to form new materials with particular morphologies according to the invention. The method of the invention can thus be used as a method for recycling used materials including the metal element or other metal elements that one wishes to incorporate into the lithium-containing oxide according to the method of the invention. For example, the method of the invention can comprise recycling used battery electrodes and thus permits the production of new electrodes from used electrodes. Furthermore, the lithium-containing oxides obtained according to the method of the invention can be recycled when they reach the end of their lifetime by means of a new method according to the invention.

The organic ligand or ligands can be used in stoichiometric quantity, or slightly in excess relative to the metal element(s). Of course, the choice of ligand or ligands is such that they can complex with the metal element or elements that one wishes to obtain in the coordination polymer.

Also, when the purpose of the method is the production of a monometal lithium-containing oxide, two methods can be used according to the selection of the ligands and metal elements present in solution during operation a1).

According to a first method, when the solution contains metal elements of different natures, the organic ligand or ligands should be selective for the metal element that one wishes to see incorporated in the coordination polymer.

According to a second method, when the solution contains a single metal element (namely, the metal element that one wishes to incorporate into the coordination polymer), the choice of ligands is greater, in that the only criterion which controls the choice of ligands is the capacity of the ligand or ligands to complex the single metal element (without requiring the strict selectivity of said metal element).

When the purpose of the method is the preparation of a multimetal lithium-containing oxide, the solution of the operation a1) contains the metal element or metal elements designed to enter the constitution of the lithium-containing oxide to which can be added:
- a single type of organic ligand reactive to all of the metal elements designed to enter the constitution of the lithium-containing oxide;
- several types of ligands, each of which is reactive to at least one of the metal elements, each of the metal elements having to be in the end complexed with at least one of the selected ligands.

Independently of the selected options, once added, the organic ligand or ligands form conventionally with the metal element or metal elements a precipitate corresponding to the coordination polymer(s) mentioned above.

The heating of operation a3) can be performed, for example at a temperature ranging from 50° ° C. to 200° C., and preferably from 80° C. to 160° C. The duration of the heating is for example from 1 hour to 48 hours, and preferably from 16 hours to 24 hours, by which the coordination polymer or polymers is/are obtained.

The invention is described in the following with reference to the following examples given by way of illustration and without limitation.

BRIEF DESCRIPTION OF THE DRAWINGS

The present invention will be better understood by referring to the following description and the accompanying figures in which:

FIGS. 1A, 2A, 3A and 4A are schematic representations of different coordination polymers, according to different embodiments of the invention;

FIGS. 1B, 2B, 3B and 4B are schematic representations of different oxides obtained after calcination of the coordination polymers represented respectively in FIGS. 1A, 2A, 3A and 4A, according to different embodiments of the invention;

FIGS. 1C, 2C, 3C and 4C show X-ray diffraction spectra of the coordination polymers represented respectively in FIGS. 1A, 2A, 3A and 4A;

FIGS. 1D, 2D, 3D and 4D show X-ray diffraction spectra of the oxides represented respectively in FIGS. 1B, 2B, 3B and 4B;

FIGS. 1E, 2E, 3E and 4E are graphs representing the capacity C (in mAh/g) as a function of the ring number N at C/10 of the oxides represented respectively in FIGS. 1B, 2B, 3B and 4B; and FIG. 1F is a graph representing the capacity C (in mAh/g) as a function of the ring number at 1C of metal oxide represented in FIG. 1B.

DETAILED DESCRIPTION OF PARTICULAR EMBODIMENTS

Example 1

Figure 3A:
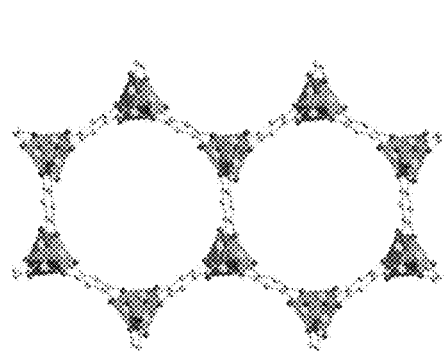

The present example relates to the synthesis of a lamellar oxide of type $Li(Ni_{1/3}Mn_{1/3}Co_{1/3})O_2$ coordination polymer with a base of 2,5-dihydroxyterephthalic acid and metal elements cobalt, nickel and manganese (this coordination polymer can be denoted MOF-74) which is reacted with lithium carbonate to form the aforementioned lithium-containing oxide.

The reaction scheme is illustrated symbolically in FIGS. 1A and 1B by representation of the coordination polymer MOF-74 and the lithium-containing oxide having different octahedral sheets 1 comprising cobalt, manganese and nickel between which infill sheets 3 of lithium ions are arranged.

To achieve this, a mixture of 0.43 g cobalt nitrate $Co(NO_3)_2*6H_2O$, 0.37 g manganese nitrate $Mn(NO_3)_2*4H_2O$ and 0.43 g nickel nitrate $Ni(NO_3)_2*6H_2O$ is dissolved in a solution comprising a mixture of 51 ml dimethylformamide, 3 mL ethanol and 3 ml water.

2,5-dihydroxyterephthalic (2,5-dhtp) acid (0.10 g) is introduced into the mixture. The solution is then decanted into an autoclave and heated to 160° C. for 24 hours. A black powder is obtained. An X-ray diffraction analysis (XRD) confirms that it is a MOF-74 $(Ni_xMn_yCo_z)_2(2,5\text{-dhtp})$, the result of this analysis being illustrated in FIG. 1C.

This material is then mixed with 0.23 g lithium carbonate (excess of 3.3% in stoichiometric ratio relative to 7.24 mmol recovered MOF-74) then is calcined at 900° C. for 24 hours.

The X-ray diffraction analysis (XRD) of the powder obtained shows lithium-containing metal oxide obtained in lamellar form $Li(Ni_{1/3}Mn_{1/3}Co_{1/3})O_2$, the result of this analysis being illustrated in FIG. 1D.

The lithium-containing oxide obtained in this way is subjected to electrochemical tests to determine the evolution of its specific capacity as a function of the number of cycles, the results being shown in FIG. 1E (for a C/10 regime) and FIG. 1F (for a 1C regime). This indicates, for a C/10 regime, a capacity ranging between 150 and 120 mAh/g between 0 and 100 cycles and, for a 1C regime, a capacity ranging between 120 and 100 mAh/g between 0 and 100 cycles. These results are the level of those obtained with a NMC type lithium-containing oxide already used in lithium batteries.

Example 2

The present example relates to the synthesis of a lamellar oxide $LiCoO_2$ from a coordination polymer based on 2-methylimidazole and cobalt (this coordination polymer can be denoted ZIF-8) which is reacted with lithium carbonate to form the aforementioned lamellar oxide.

The reaction scheme is illustrated symbolically in FIGS. 2A and 2B by representation of the coordination polymer ZIF 8 in FIG. 2A and, in FIG. 2B, of lithium-containing oxide having different octahedral sheets 5 comprising cobalt between which infill sheets 7 of lithium ions are arranged.

To achieve this, a mixture of 2.8 g cobalt nitrate $Co(NO_3)_2*6H_2O$ and 5.9 g 2-methylimidazole is mixed with 60 mL methanol. After dissolving cobalt nitrate, the mixture is then placed into an autoclave which is heated at 100° C. for 16 hours. A violet powder is produced. An X-ray diffraction analysis (XRD) confirms that it is a type ZIF-8 coordination polymer, the result of this analysis being illustrated in FIG. 2C.

300 mg of this material is then mixed with 52.6 g $Li_2CO_3$ (excess of 3.3% in stoichiometric ratio) then is calcined at 850° C. for 24 hours.

The X-ray diffraction analysis (XRD) of the powder obtained shows the production of a lithium-containing metal oxide in the form of lamellar $LiCoO_2$, the result of this analysis being illustrated in FIG. 2D.

The lithium-containing oxide obtained in this way is subjected to electrochemical tests, so as to determine its specific capacity, the results being presented in FIG. 2E (for a C/10 regime). This indicates an initial specific capacity of 120 mAh/g.

Example 3

The present example relates to the synthesis of a lamellar oxide of type $LiMn_2O_4$ from a coordination polymer based on 2,5-dihydroxyterephthalic acid and manganese (this coordination polymer can be denoted MOF-74) which is reacted with lithium carbonate to form the aforementioned lithium-containing oxide.

Figure 3B:
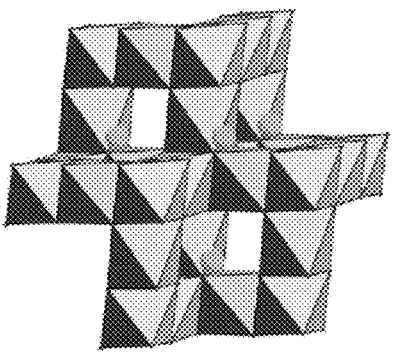

The reaction scheme is illustrated symbolically in FIGS. 3A and 3B by representation of the coordination polymer MOF-74 and the spinel structure lithium-containing oxide.

Figure 3C:
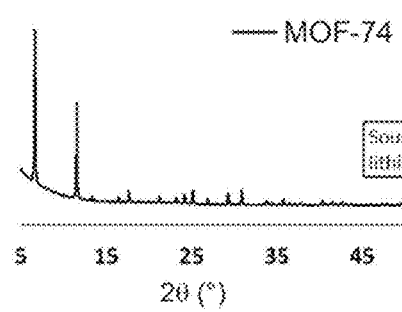

To achieve this, 1.37 g $Mn(NO_3)_2*4H_2O$ is dissolved in a solution comprising 55 ml dimethylformamide and 2.5 ml water. To that, 2,5-dihydroxyterephthalic acid (0.56 g in 2.5 ml water) is introduced into the mixture. The solution is then decanted into an autoclave then heated to 160° C. for 24 hours. An X-ray diffraction analysis (XRD) confirms that it is a MOF-74 type coordination polymer, the result of this analysis being illustrated in FIG. 3C.

300 mg of this material is then mixed with 19.1 mg lithium carbonate (excess of 3.3% in stoichiometric ratio) then is calcined at 800° C. for 12 hours.

Figure 3D:
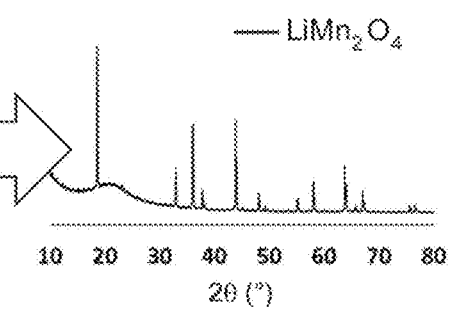

X-ray diffraction analysis of the powder obtained shows obtaining a spinel phase of $LiMn_2O_4$, as shown in FIG. 3D.

Figure 3E:
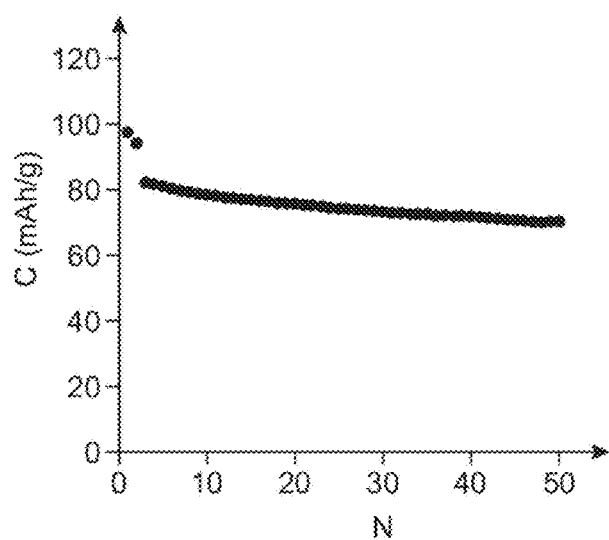

The lithium-containing oxide obtained in this way is subjected to electrochemical tests, so as to determine its specific capacity, the results being presented in FIG. 3E (for a C/10 regime). This results in an initial specific capacity of 100 mAh/g.

Example 4

The present example relates to the synthesis of a lamellar oxide $LiCoO_2$ from a coordination polymer based on 2,5-dihydroxyterephthalic acid and cobalt (this coordination polymer can be denoted MOF-74) which is reacted with lithium carbonate for forming the aforementioned lithium-containing oxide.

Figure 4A:
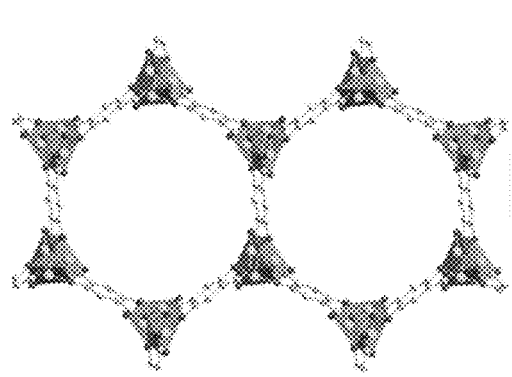
Figure 4B:
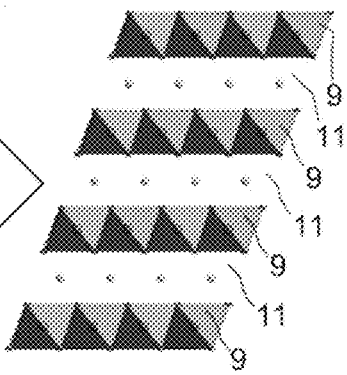

The reaction scheme is illustrated symbolically in FIGS. 4A and 4B by representation of the coordination polymer MOF-74 and lamellar lithium-containing oxide having different octahedral sheets 9 comprising cobalt between which infill sheets 11 of lithium ions are arranged.

Figure 4C:
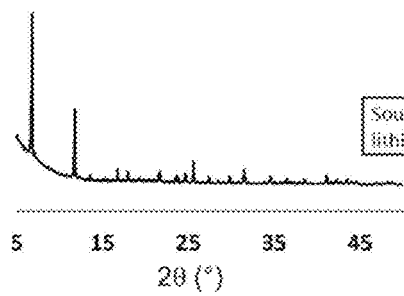

To achieve this, 1.62 g cobalt nitrate $Co(NO_3)_2*6H_2O$ is dissolved in a solution comprising 55 ml dimethylformamide and 2.5 mL water. To that, 2,5-dihydroxyterephthalic acid (0.56 g in 2.5 ml water) is introduced into the mixture. The solution is then decanted into an autoclave then heated at 160° C. for 24 hours. An X-ray diffraction analysis (XRD) confirms that it is a MOF-74 type coordination polymer, the result of this analysis being illustrated in FIG. 4C.

300 mg of this material is then mixed with 37.3 mg lithium carbonate (excess of 3.3% in stoichiometric ratio) then is calcined at 800° C. for 12 hours.

Figure 4D:
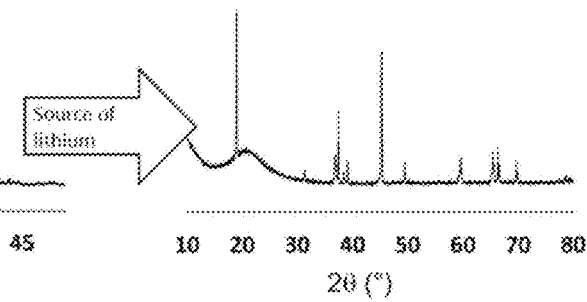

The X-ray diffraction analysis (XRD) of the powder obtained shows the formation of a lithium-containing metal oxide in the form of lamellar $LiCoO_2$, the result of this analysis being illustrated in FIG. 4D.

Figure 4E:
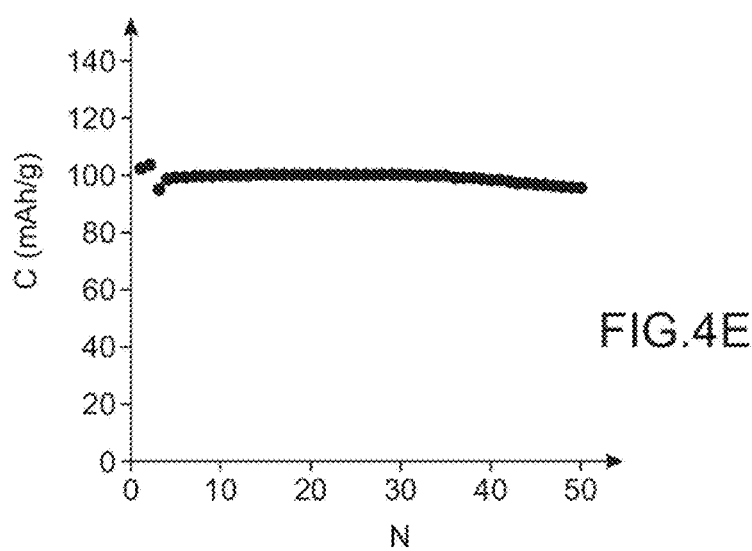

The lithium-containing oxide obtained in this way is subjected to electrochemical tests, so as to determine the evolution of its specific capacity as a function of the number of cycles, the results being presented in FIG. 4E (for a C/10 regime). This indicates an initial specific capacity of 105 mAh/g, which remains stable for at least 50 cycles.

What is claimed is:

1. Method for producing a lithium-containing oxide comprising one or more other metal elements comprising the following successive steps:
   a) a step of contacting at least one coordination polymer comprising an organic part and the metal element or other metal elements bonded to one another by organic ligands with a lithium source;
   b) a single step of calcination of the mixture produced from step a), whereby the suppression of the organic part of the coordination polymer and the formation of the lithium-containing oxide are obtained.

2. Method according to claim 1, wherein the metal element or other metal elements are selected from transition metal elements, post-transition metal elements and mixtures of the latter.

3. Method according to claim 1, wherein the metal element or other metal elements are selected from manganese, cobalt, nickel and mixtures thereof.

4. Method according to claim 1, wherein the organic ligands comprise at least two groups establishing coordination bonds with the metal element or other metal elements.

5. Method according to claim 1, wherein the organic ligands are:
   organic ligands comprising at least two groups selected from —COOR groups, —OH groups and combinations thereof, with R representing a hydrogen atom or a monovalent cation;
   organic ligands consisting of aromatic compounds comprising at least one ring comprising at least two nitrogen atoms; or
   mixtures thereof.

6. Method according to claim 1, wherein the organic ligands are aromatic compounds comprising at least one ring comprising at least two groups selected from —COOR groups, OH groups and combinations thereof, with R representing a hydrogen atom or a monovalent cation.

7. Method according to claim 6, wherein the organic ligands are ligands from the family of hydroxyterephthalic acids.

8. Method according to claim 6, wherein the coordination polymer is a coordination polymer comprising at least one metal element selected from cobalt, nickel, manganese and mixtures thereof, the metal elements being bonded to one another by organic ligand, wherein the organic ligand is:
- an organic ligand comprising at least two groups selected from —COOR groups, —OH groups and combinations thereof, with R representing a hydrogen atom or a monovalent cation;
- an organic ligand consisting of aromatic compounds comprising at least one ring comprising at least two nitrogen atoms;
- an aromatic compound comprising at least one ring comprising at least two groups selected from —COOR groups, OH groups and combinations thereof, with R representing a hydrogen atom or a monovalent cation; or
- mixtures thereof.

9. Method according to claim 1, wherein the organic ligands are:
- monocyclic aromatic compounds with five members comprising two nitrogen atoms;
- bicyclic aromatic compounds, where one ring is a ring with five members comprising two nitrogen atoms;
- monocyclic aromatic compounds with six members comprising two nitrogen atoms or three nitrogen atoms; or
- mixtures of the latter.

10. Method according to claim 9, wherein the organic ligands are imidazole compounds corresponding to at least of the following formulae (II) to (V):

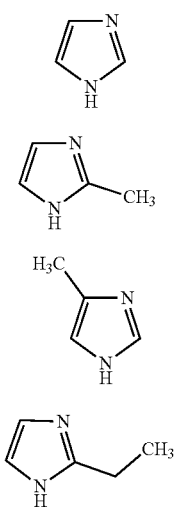

(II)

(III)

(IV)

(V)

11. Method according to claim 9, wherein the organic ligands are benzimidazole compounds.

12. Method according to claim 9, wherein the organic ligands are compounds corresponding to one of the formulae (VII) to (IX):

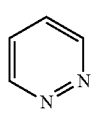

(VII)

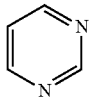

(VIII)

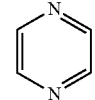

(IX)

13. Method according to claim 9, wherein the organic ligands are compounds according to one of the following formulae (X) to (XII):

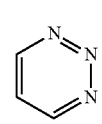

(X)

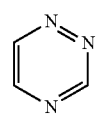

(XI)

(XII)

14. Method according to claim 9, wherein the coordination polymer is a coordination polymer comprising cobalt and organic ligands, wherein the organic ligands are:
- monocyclic aromatic compounds with five members comprising two nitrogen atoms;
- bicyclic aromatic compounds, where one ring is a ring with five members comprising two nitrogen atoms;
- monocyclic aromatic compounds with six members comprising two nitrogen atoms or three nitrogen atoms; or
- mixtures of the latter.

15. Method according to claim 1, wherein the source of lithium is lithium carbonate, lithium hydroxide or lithium acetate.

16. Method according to claim 1, wherein the calcination step is performed at a temperature ranging from 700° C. to 1000° C. for a duration ranging from 12 hours to 24 hours.

17. Method according to claim 1, also comprising a step of preparing the coordination polymer or polymers used in step a).

18. Method according to claim 1, wherein the lithium-containing oxide is either a lamellar lithium-containing oxide of formula $LiMO_2$, where M is chosen from Co, Ni, Mn, Al and mixtures thereof, or a lithium-containing oxide with a spinel structure.

19. Method according to claim 18, wherein the lamellar lithium-containing oxide of formula $LiMO_2$ is $LiCoO_2$, $LiNiO_2$, $Li(Ni,Mn,Co)O_2$ or $Li(Ni,Co,Mn,Al)O_2$.

20. Method according to claim 18, wherein the lithium-containing oxide with a spinel structure is $LiMn_2O_4$.

* * * * *